United States Patent
Biber

(10) Patent No.: US 6,254,046 B1
(45) Date of Patent: Jul. 3, 2001

(54) SUPPORT HAVING AN ADJUSTING DEVICE

(75) Inventor: Klaus Biber, Aalen (DE)

(73) Assignee: Carl-Zeiss-Stiftung, Heidenheim (DE)

( * ) Notice: Subject to any disclaimer, the term of this patent is extended or adjusted under 35 U.S.C. 154(b) by 0 days.

(21) Appl. No.: 09/234,221

(22) Filed: Jan. 19, 1999

(30) Foreign Application Priority Data

Jan. 19, 1998 (DE) .............................................. 198 01 571

(51) Int. Cl.$^7$ .................................................. E04G 3/00
(52) U.S. Cl. ........................................ 248/287.1; 248/913
(58) Field of Search .............................. 248/279.1, 274.1, 248/284.1, 286.1, 285.51, 224.1, 287.1, 178, 476, 913, 288.11, 298.1, 296.1, 291.1, 288.31, 124.1, 124.2, 123.11, 288.51, 12.8; 425/141, 367

(56) References Cited

U.S. PATENT DOCUMENTS

| | | | |
|---|---|---|---|
| 3,585,878 | * | 6/1971 | Heckenbach, Jr. ..................... 74/675 |
| 3,891,301 | * | 6/1975 | Heller ..................................... 350/85 |
| 4,344,595 | * | 8/1982 | Heller et al. .................. 248/280.1 X |
| 5,005,906 | * | 4/1991 | Suzuki et al. ......................... 297/362 |
| 5,029,791 | * | 7/1991 | Ceccon et al. ........................ 248/287 |
| 5,058,840 | * | 10/1991 | Moss et al. ........................ 248/118.5 |
| 5,288,043 | * | 2/1994 | Tigliev ............................... 248/123.1 |
| 5,295,803 | * | 3/1994 | Ogawa et al. ........................ 425/141 |
| 5,443,237 | * | 8/1995 | Stadtmauer ................... 248/118.3 X |
| 5,609,316 | * | 3/1997 | Tigliev ............................. 248/123.11 |
| 5,667,186 | * | 9/1997 | Luber et al. ................. 248/297.11 X |
| 5,752,683 | * | 5/1998 | Novis et al. ................... 248/279.1 X |
| 5,760,500 | * | 6/1998 | Kondo et al. .................... 248/913 X |
| 5,765,273 | * | 6/1998 | Mora et al. ................... 248/279.1 X |
| 5,842,962 | * | 12/1998 | Yamada et al. ........................ 492/18 |

* cited by examiner

Primary Examiner—Leslie A. Braun
Assistant Examiner—Tan Le
(74) Attorney, Agent, or Firm—Walter Ottesen

(57) ABSTRACT

The invention is directed to a support (1) for an apparatus (3) which is to be suspended so as to be movable. The support (1) includes a holding arm (17) and an adjusting unit (19) mounted on the holding arm (17). The adjusting device (19) includes a slidingly displaceable sliding disc (25).

14 Claims, 2 Drawing Sheets

SUPPORT HAVING AN ADJUSTING DEVICE

FIELD OF THE INVENTION

The invention relates to a support for an apparatus which is suspended and movable. The support has a holding arm and an adjusting device mounted on the holding arm. The apparatus can be mounted on the adjusting device and can be shifted relative to the holding arm.

BACKGROUND OF THE INVENTION

A support of this kind and an adjusting unit are disclosed, for example, in European patent publication 0,433,426. This support carries an apparatus in the form of a surgical microscope and the adjusting unit is mounted between a holding arm of the support and the surgical microscope. The surgical microscope can be shifted relative to the holding arm with the adjusting unit. In this way, the center of gravity of the surgical microscope can be shifted relative to the support in order to balance the entire system.

A further support is disclosed in German patent publication 3,147,836. In this publication, the gearing system of the adjusting unit is shown in detail. Here, an adjusting unit includes a cross-slide guide with self-arrestment. It can be seen that the adjusting device is configured so as to be constructively complex.

SUMMARY OF THE INVENTION

It is an object of the invention to provide a support having an adjusting unit which is simpler and more cost-effective to manufacture without suffering any diminishment of function.

The support of the invention is for an apparatus which is suspended and movable. The support includes: a holding arm; an adjusting unit on which the apparatus can be mounted and displaced relative to the holding arm; and, the adjusting unit including a slidably displaceable slide disc.

With the above measure, the known threaded rod guidance having two mutually orthogonal guide spindles can be omitted and yet provide expanded adjusting possibilities. The known threaded rod guidance requires a mutual engagement of threads of spindles and displacing elements.

The slide disc is slidably guided or slidably displaced. Because of this slide disc, the adjusting directions in which the apparatus, which is suspended on the support, can be directly displaced, are not limited to the directions which are fixedly pregiven by the guide spindles. Rather, the slide disc can basically be displaced in a plurality of adjusting directions within the slide plane.

In one embodiment, the slide disc is displaceable in a slide housing. In this way, an especially precise and tolerance-free support of the slide disc is achieved. The slide disc can be connected either to the holding arm or to the apparatus.

The slide disc can be connected to the apparatus and the slide housing, which surrounds the slide disc, can be connected to the holding arm. If this is the case, then the slide disc is moved with the apparatus for an adjustment of the apparatus whereby the mass inertia, which is to be overcome, can be relatively small.

In a further embodiment, the slide disc is guided in a slide plane by at least two slide bearings extending on both sides of the slide plane. With this measure, a tilt-free and rocking-free support of the slide disc is achieved and therefore, a precise adjustability of the apparatus, which is as free of play as possible, is achieved. Furthermore, with the adjustment or displacement of these slide bearings, the slide resistance and/or the play of the slide disc can be adjusted in the slide housing.

The degrees of adjustment of the apparatus with respect to an especially clear adjustment method of the apparatus can be limited when the apparatus is guided within the slide plane via slide guides.

Here, the slide disc can be guided in two mutually perpendicular directions via crossed slide guides and therefore the usually X/Y-adjustability of the apparatus is realized.

With respect to a precise positioning of the apparatus, it is advantageous to move the slide disc with at least two threaded spindles, which do not have to fulfill any function to guide the slide disc. The spindles are supported between the slide disc and the slide housing.

The two slide spindles can also effect an X/Y-adjustability of the apparatus when the threaded spindles are supported via roller bearings on a slide housing region parallel to the longitudinal axis of the particular other threaded spindle.

The above embodiment of the invention, is advantageous especially in combination with pressure springs which are assigned to each of the threaded spindles and are supported between the slide disc and the slide housing. This is so because the pressure springs make possible a position-stable support of the slide disc and therefore of the apparatus. This is especially so when the pressure springs are arranged in pairs symmetrically with respect to the longitudinal axis of a threaded spindle. In this way, the self-arrestment can be omitted, which is relatively complex to achieve and is inherent in the guide spindle guidance of the state of the art.

If one or more of the guide spindles are driven by a motor mounted in the slide disc, then the entire adjusting unit can be very compact because the slide housing must only be configured as a housing shell surrounding the slide disc. Accordingly, space is available within the slide disc. The slide disc exhibits a certain extension in the slide plane so as to be free of tilting and rocking.

In addition to the stand with an adjusting unit, the invention is directed also to an adjusting unit which, for example, can be used as an independent retrofit and has the corresponding adjusting unit features of the support of the invention.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
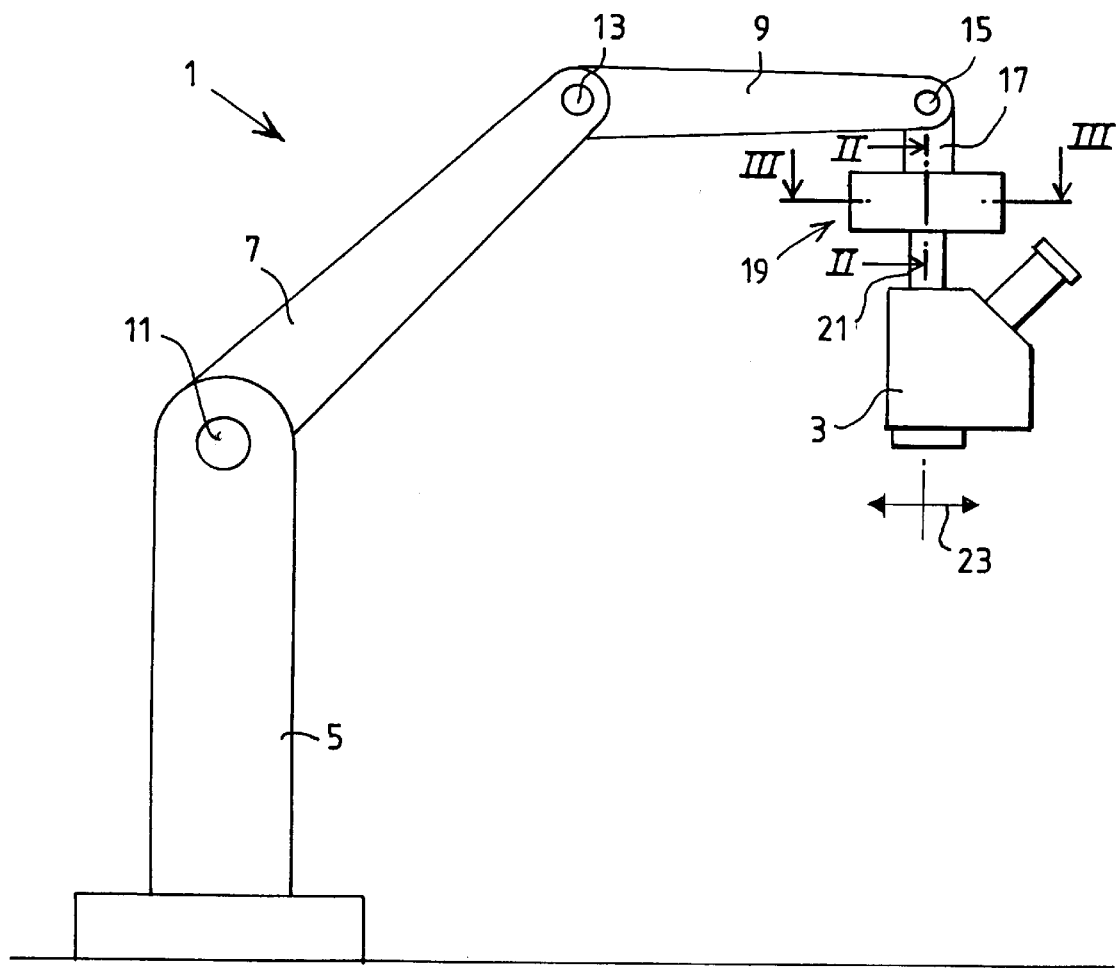
FIG. 1 is a schematic representation of a support of the invention.

In FIG. 1, a support 1 is shown on which an apparatus in the form of a surgical microscope 3 is suspended. The support 1 is shown schematically and includes support arms 5, 7 and 9 which are movably connected to each other via movable joints 11 and 13. The support arm 9 is connected to a holding arm 17 via a movable joint 15.

An adjusting unit 19 is mounted between the holding arm 17 and the surgical microscope 3. With the adjusting unit 19, the surgical microscope 3 can be mounted on the support 1 and be shifted relative to the holding arm 17, for example, in order to bring the center of gravity of the surgical microscope 3 into a specific position relative to the components of the support 1.

The surgical microscope together with an intermediate piece 21 can be shifted via the adjusting unit 19 in the X-direction and in the directions orthogonal to the plane of the drawing. The X-direction is shown by the double arrow 23. The adjusting unit 19 is shown in section in FIG. 2.

A slide disc 25 can be displaced in a slide housing 27 of the adjusting unit 19 within a slide plane shown by the dash-dot line 29. Here, it can be seen that the intermediate piece 21 is fixedly connected to the slide disc 25 and extends through a circularly-shaped recess 28 of the slide housing with play to allow movement.

The slide disc 25 can be displaced in the slide plane 29 with especially low friction via the slide bearings 31, 33, 35 and 37. The slide bearings 31 and 33 extend on the side of the slide plane 29 facing toward the support and the slide bearings 35 and 37 extend on the side of the slide plane 29 facing toward the surgical microscope 3.

A threaded spindle 41 is supported between a slide housing region 39 and the slide disc 25 and serves to move the slide disc 25 and therefore the surgical microscope 3 relative to the holding arm 17 of the support 1.

The threaded spindle 41 is rotated by a motor 43 mounted in the slide disc 25 and thereby displaces a threaded nut 45 which is supported by a roller bearing 47 against the slide housing region 39. The threaded nut 45 is close to the slide housing and is secured against rotation by planar contact against the inner wall of the slide housing close to the support arm.

Figure 2:
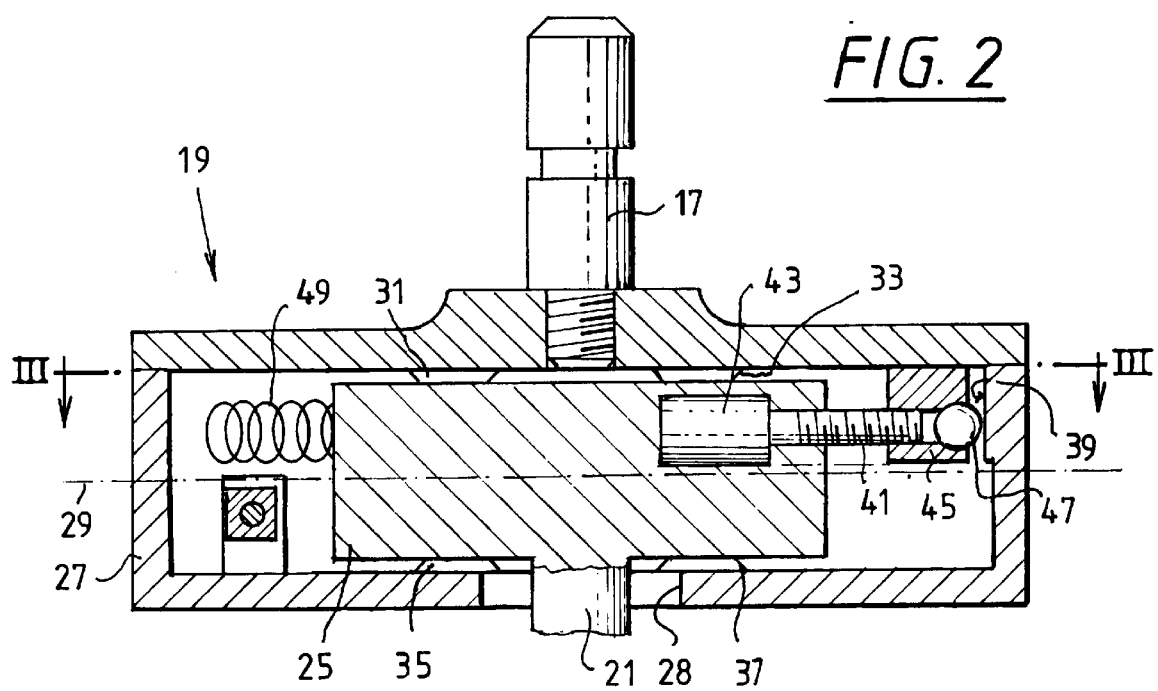
FIG. 2 is a section view of the adjusting unit mounted on the support shown in FIG. 1 as seen in the direction of arrows II of FIG. 1; and, FIG. 3 is a section view of the adjusting unit of FIG. 1 as seen in the direction of arrows III of FIGS. 1 and 2.
Figure 3:
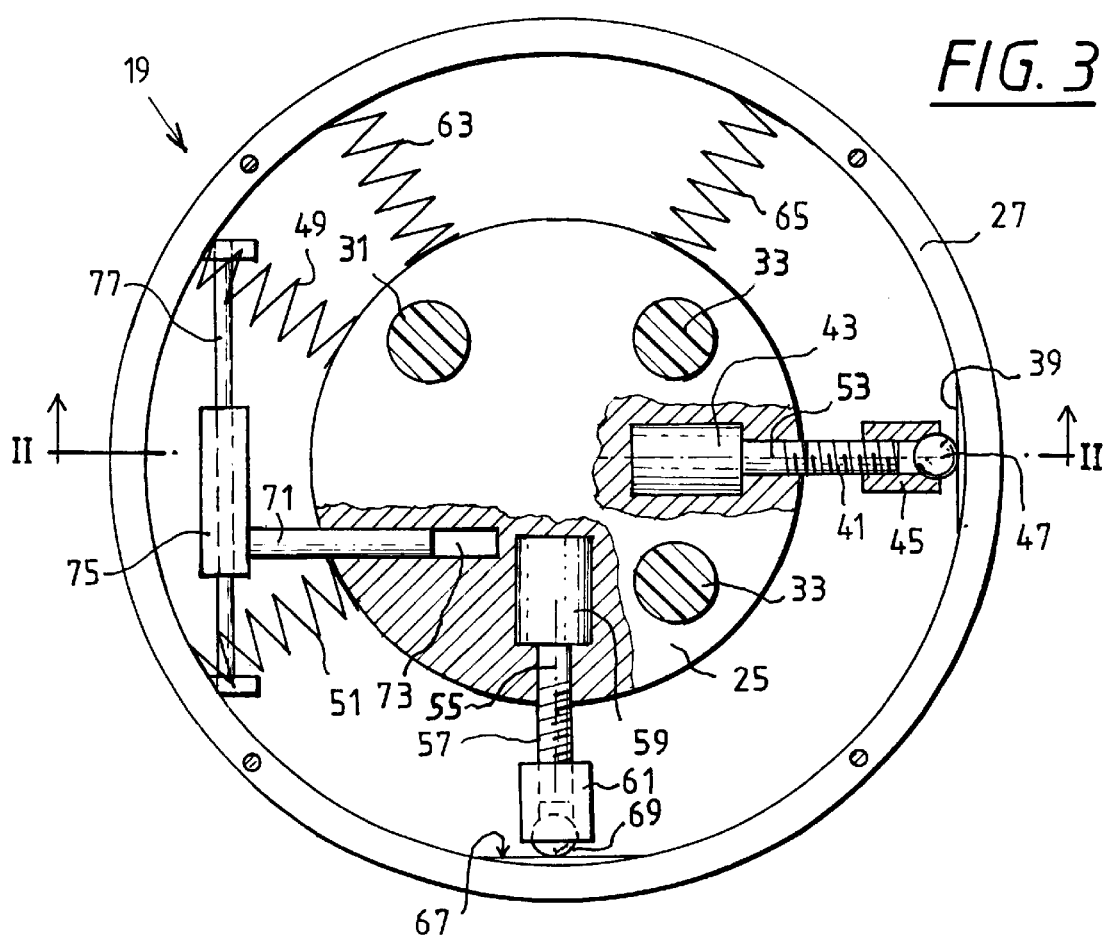

In FIG. 3, the adjusting unit 19 is shown in section orthogonally to the section view of FIG. 2.

In FIG. 3, it can be seen that pressure springs 49 and 51 are assigned to the threaded spindle 41. The pressure springs 49 and 51 are arranged symmetrically with respect to the longitudinal axis 53 of the threaded spindle 41 in order to hold the slide disc 25 together with threaded spindle 41 always in a stable equilibrium position. The longitudinal axis 53 is parallel to the X-direction.

A further threaded spindle 57 is aligned with its longitudinal axis orthogonally to the threaded spindle 41 and is mounted in the adjusting unit 19 for a defined shift of the slide disc 25. The longitudinal axis of the threaded spindle 57 is parallel to the Y-direction. The threaded spindle 57 is rotated by a motor 59 mounted in the slide disc 25 and can displace the slide disc 25 along its longitudinal axis 55 by coaction with the nut 61 which is held so that it cannot rotate.

Pressure springs 63 and 65 are assigned to the threaded spindle 57 and are arranged symmetrically with respect to the longitudinal axis 55 of the spindle. The pressure springs 63 and 65 are supported on the side of the disc 25 lying opposite to the threaded spindle 57 and are supported between the slide disc 25 and the slide housing 27.

The slide housing region 39 is parallel to the Y-direction in order the hold the X-position of the slide disc 25 constant in a simple manner during a displacement in the Y-direction.

In the same manner, the housing region 67 is parallel to the X-direction. This housing region 67 coacts with a roller bearing 69 which rolls on the slide housing region 67 during a displacement of the slide disc 25 in the direction of the longitudinal axis 53. The threaded spindle nut 61 is supported on the slide housing 27 so as to be secure against rotation via the roller bearing 69.

The adjusting region is defined via a special configuration of the slide housing regions 39 and 67 and provides a constructive simple decoupling of a shift in the X-direction from a shift in the Y-direction. This adjusting region is delimited by slide disc stops (not shown) in the slide housing 27.

The motors 59 and 43 can also be mounted in the slide housing.

A hollow cylindrical recess 73 is formed in the slide disc 25 and a cylindrical rod 71 extends in the X-direction. The slide disc 25 is guided in the X-direction by the sliding engagement of the rod 71 in the recess 73.

The rod 71 is fixedly connected to a sleeve 75 at its end remote from the slide disc. The sleeve 75 slides on a cylindrical rod 77 which is fixedly connected to the slide housing 27 and extends in the Y-direction. In this way, the slide disc 25 is guided in the Y-direction.

It is understood that the foregoing description is that of the preferred embodiments of the invention and that various changes and modifications may be made thereto without departing from the spirit and scope of the invention as defined in the appended claims.

What is claimed is:

1. A support for an apparatus which is suspended and movable, the support comprising:

a holding arm;

an adjusting unit on which said apparatus can be mounted and displaced relative to said holding arm;

said adjusting unit including a slidably displaceable slide disc;

said adjusting unit including a slide housing and said slide disc being displaceably mounted in said slide housing;

said slide housing being connected to said holding arm and said apparatus being connectable to said slide disc;

said slide housing defining a slide plane and said slide housing and said slide disc conjointly defining first and second interfaces on respective sides of said slide plane; and said adjusting unit further including respective sets of slide bearings at said first and second interfaces.

2. The support of claim 1, said adjusting unit further including a slide guidance arrangement for guiding said slide disc in said slide plane.

3. The support of claim 2, said slide guidance arrangement including mutually crossed first and second guidance units for guiding said slide disc in two mutually orthogonal directions.

4. The support of claim 3, said adjusting unit further comprising first and second threaded spindle units for displacing said slide disc in said directions, respectively; and said first and second threaded spindle units including first and second threaded spindles, respectively, which are braced between said slide housing and said slide disc.

5. The support of claim 4, said first and second threaded spindles defining first and second longitudinal axes, respectively; said slide housing defining first and second contact regions for coacting with said first and second threaded spindles, respectively; and said first contact region being parallel to said second longitudinal axis and said second contact region being parallel to said first longitudinal axis; and said first and second threaded spindle units including: first and second roller bearings for supporting said first and second threaded spindles, respectively, against corresponding ones of said contact regions.

6. The support of claim 5, each of said threaded spindle units comprising a set of pressure springs arranged symmetrically with respect to the longitudinal axis of the threaded spindle corresponding thereto and arranged braced in opposition thereto.

7. The support of claim 6, each of said threaded spindle units including a motor mounted in said slide disc for driving the threaded spindle corresponding thereto.

8. An adjusting unit on which an apparatus can be mounted and displaced, the adjusting unit comprising a slidably displaceable slide disc;

said adjusting unit including a slide housing and said slide disc being displaceably mounted in said slide housing;

said apparatus being connectable to said slide disc;

said slide housing defining a slide plane and said slide housing and said slide disc conjointly defining first and second interfaces on respective sides of said slide plane; and said adjusting unit further including respective sets of slide bearings at said first and second interfaces.

9. The adjusting unit of claim 8, said adjusting unit further including a slide guidance arrangement for guiding said slide disc in said slide plane.

10. The adjusting unit of claim 9, said slide guidance arrangement including mutually crossed first and second guidance units for guiding said slide disc in two mutually orthogonal directions.

11. The adjusting unit of claim 10, said adjusting unit further comprising first and second threaded spindle units for displacing said slide disc in said directions, respectively; and said first and second threaded spindle units including first and second threaded spindles, respectively, which are braced between said slide housing and said slide disc.

12. The adjusting unit of claim 11, said first and second threaded spindles defining first and second longitudinal axes, respectively; said slide housing defining first and second contact regions for coacting with said first and second threaded spindles, respectively; and said first contact region being parallel to said second longitudinal axis and said second contact region being parallel to said first longitudinal axis; and, said first and second threaded spindle units including: first and second roller bearings for supporting said first and second threaded spindles, respectively, against corresponding ones of said contact regions.

13. The adjusting unit of claim 12, each of said threaded spindle units comprising a set of pressure springs arranged symmetrically with respect to the longitudinal axis of the threaded spindle corresponding thereto and arranged braced in opposition thereto.

14. The adjusting unit of claim 13, each of said threaded spindle units including a motor mounted in said slide disc for driving the threaded spindle corresponding thereto.

* * * * *